United States Patent [19]

Müller-Gliemann et al.

[11] Patent Number: 5,607,962

[45] Date of Patent: Mar. 4, 1997

[54] SUBSTITUTED INDOLE DERIVATIVES

[75] Inventors: Matthias Müller-Gliemann, Solingen; Ulrich Müller, Wuppertal, both of Germany; Martin Beuck, Milford, Conn.; Siegfried Zaiss, Wuppertal, Germany; Christoph Gerdes, Leverkusen, Germany; Anke Domdey-Bette, Hückeswagen, Germany; Rudi Grützmann, Solingen, Germany; Stefan Lohmer, Milan, Italy; Stefan Wohlfeil, Hilden, Germany; Özkan Yalkinoglu, Wuppertal, Germany; James Elting, Madison, Conn.; Dirk Denzer, Wuppertal, Germany

[73] Assignee: Bayer Aktiengesellschaft, Leverkusen, Germany

[21] Appl. No.: 591,329

[22] Filed: Jan. 25, 1996

[30] Foreign Application Priority Data

Feb. 1, 1995 [DE] Germany .................. 195 03 159.8
Apr. 11, 1995 [DE] Germany .................. 195 13 176.7

[51] Int. Cl.$^6$ .................. A61K 31/40; C07D 209/24
[52] U.S. Cl. .................................. 514/415; 548/506
[58] Field of Search .................. 514/415; 548/506

[56] References Cited

U.S. PATENT DOCUMENTS 5,380,722  1/1995  Clemence et al. .................. 514/415
5,395,840  3/1995  Muller et al. .

FOREIGN PATENT DOCUMENTS 397210  11/1990  European Pat. Off. .
9418968  9/1994  WIPO .

OTHER PUBLICATIONS

The Journal of Cell Biology, vol. 50, pp. 172 to 186, Russell Ross, "The Smooth Muscle Cell", 1971.
Laboratory Investigation, vol. 32, No. 3, p. 339, Jay A. Fishman, et al., 1975.

*Primary Examiner*—Patricia L. Morris
*Attorney, Agent, or Firm*—Sprung Horn Kramer & Woods

[57] ABSTRACT

Substituted indole derivatives are prepared by reacting appropriate carboxylic acids, if appropriate in the presence of auxiliaries, with appropriate amines. The substituted indole derivatives are suitable as active compounds in medicaments, in particular in medicaments for the treatment of arteriosclerosis and restenosis.

7 Claims, No Drawings

SUBSTITUTED INDOLE DERIVATIVES

The invention relates to indole derivatives, processes for their preparation, and their use in medicaments, in particular for the treatment of arteriosclerosis and restenosis.

The present invention relates to substituted indole derivatives of the general formula (I)

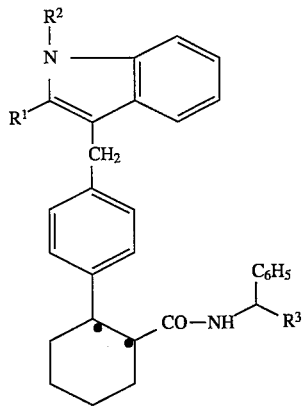

in which
- $R^1$ represents phenyl, cycloalkyl having 3 to 6 carbon atoms or straight-chain or branched alkyl having up to 5 carbon atoms,
- $R^2$ represents straight-chain or branched alkyl having up to 8 carbon atoms, or hydrogen,
- $R^3$ represents a radical of the formula $-CO-NH_2$ or $-CH_2-OH$, and their salts.

The substituted indole derivatives according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred salts are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms, which either behave as image and mirror image (enantiomers), or which do not behave as image and mirror image (diastereomers). The invention relates both to the enantiomers or diastereomers or their respective mixtures. Like the diastereomers, the racemic forms can also be separated into the stereoisomerically uniform constituents in a known manner.

Preferred compounds of the general formula (I) are those in which
- $R^1$ represents phenyl, cyclopropyl, cyclopentyl, cyclohexyl or straight-chain or branched alkyl having up to 4 carbon atoms,
- $R^2$ represents straight-chain or branched alkyl having up to 6 carbon atoms, or hydrogen,
- $R^3$ represents a radical of the formula $-CO-NH_2$ or $-CH_2-OH$, and their salts.

Particularly preferred compounds of the general formula (I) are those
in which
- $R^1$ represents phenyl, cyclopropyl, ethyl, iso-propyl or n-butyl,
- $R^2$ represents straight-chain or branched alkyl having up to 5 carbon atoms, or hydrogen,
- $R^3$ represents a radical of the formula $-CO-NH_2$ or $-CH_2-OH$, and their salts.

The compounds of the general formula (I) according to the invention are prepared by hydrolysing compounds of the general formula (II)

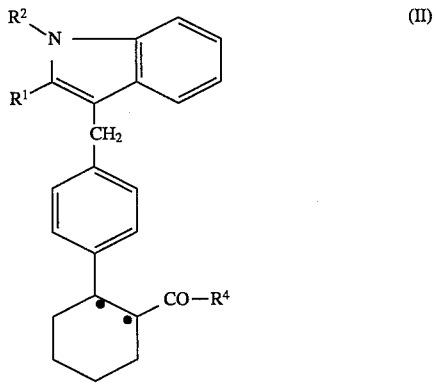

in which
$R^1$ and $R^2$ have the meaning indicated,
and
$R^4$ represents straight-chain or branched $C_1$–$C_4$-alkoxy or hydroxyl and reacting the acid, if appropriate with prior activation, in inert solvents, in the presence of a base and/or of a dehydrating agent, with phenylglycine derivatives of the general formula (III)

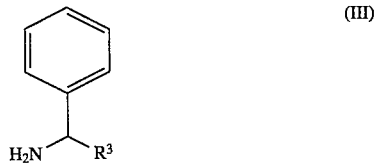

in which
$R^3$ has the meaning indicated.

The process according to the invention can be illustrated by way of example by the following reaction scheme:

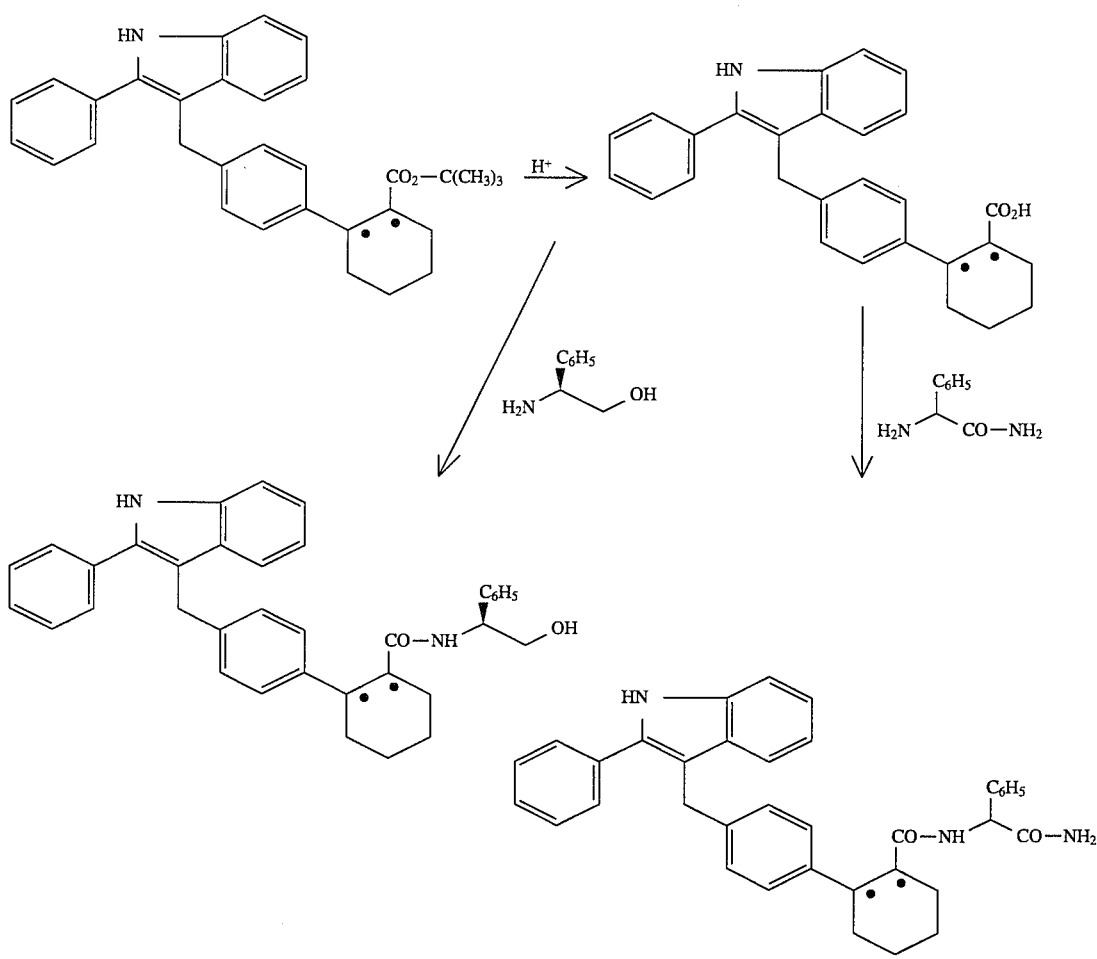

Suitable solvents for the process are customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Dichloromethane, tetrahydrofuran and dimethylformamide are preferred.

In general, bases which can be employed for the process according to the invention are inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate, potassium carbonate or caesium carbonate, alkaline earth metal carbonates such as calcium carbonate, or alkali metal or alkaline earth metal alkoxides such as sodium or potassium methoxide, sodium or potassium ethoxide or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals such as sodium or their hydrides such as sodium hydride as bases. Sodium hydride, potassium carbonate, triethylamine, trimethylamine, pyridine, potassium tert-butoxide, DBU or DABCO are preferred.

In general, the base is employed in an amount from 0.05 mol to 10 mol, preferably from 1 mol to 2 mol, relative to 1 mol of the compound of the formula (II).

The process according to the invention is in general carried out in a temperature range from –50° C. to +100° C., preferably from –30° C. to +60° C.

The process according to the invention is in general carried out at normal pressure. However, it is also possible to carry out the process at elevated pressure or at reduced pressure (e.g. in a range from 0.5 to 5 bar).

The amidation can optionally proceed via the activated stage of the acid halides or mixed anhydrides, which can be prepared from the corresponding acids by reaction with thionyl chloride, phosphorus trichloride, phosphorus pentachloride, phosphorus tribromide or oxalyl chloride or methanesulphonyl chloride.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride, or carbonyl compounds such as carbonyldiimidazole, or 1,2-oxazolium compounds such as 2-ethyl-5-phenyl -1,2-oxazolium-3-sulphonate, or propanephosphonic anhydride or isobutyl chloroformate or benzotriazolyloxy-tris-(dimethylamino)phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide.

The compounds of the formula (II) are new and are prepared by reacting compounds of the general formula (IV)

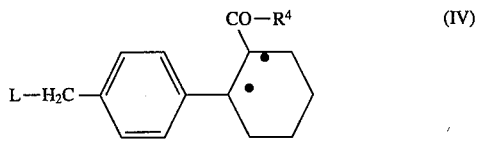

in which

L represents a typical leaving group such as, for example, chlorine, bromine, iodine, tosylate or mesylate, preferably bromine,
and $R^4$ represents straight-chain or branched $C_1$–$C_4$-alkoxy or carboxyl,
fast with compounds of the general formula (V)

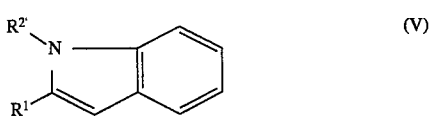

in which $R^1$ has the meaning indicated above,
and $R^{2'}$ represents hydrogen,
in inert solvents, if appropriate in the presence of a base, and, if $R^2 \neq H$, following by an alkylation according to customary methods.

The solvents and bases used can be the solvents and bases indicated above; dimethylformamide and potassium tert-butoxide are preferred.

The alkylation is in general carried out in one of the abovementioned solvents, preferably dimethylformamide, using $C_1$–$C_8$-alkyl halides, preferably iodides, in a temperature range from 0° C. to room temperature and at normal pressure.

The compounds of the formulae (III), (IV) and (V) are known per se.

The compounds of the general formula (I) according to the invention show an unforeseeable, useful spectrum of pharmacological action.

Surprisingly, they inhibit the proliferation of smooth muscle cells. They can therefore be employed for the treatment of arteriosclerosis and of restenosis.

Investigation of the inhibition of the proliferation of smooth muscle cells by the compounds according to the invention To determine the antiproliferative action of the compounds, smooth muscle cells are used which have been obtained from the aortas of pigs by the media explant technique [R. Ross, J. Cell. Biol. 50, 172, 1971]. The cells are inoculated into suitable culture dishes, as a role 96-hole plates, and cultured at 37° C. for 2–3 days in medium 199 with 7.5% FCS and 7.5% NCS, 2 mM L-glutamine and 15 mM HEPES, pH 7.4 in 5% $CO_2$. The cells are then synchronized by withdrawal of serum for 2–3 days and then stimulated to growth using serum or other factors. At the same time, test compounds are added. After 16–20 hours, $^3$H-thymidine is added and after a further 4 hours the incorporation of this substance into the TCA-precipitatable DNA of the cells is determine. To determine the $IC_{50}$ values, the active compound concentration is calculated at which sequential dilution of the active compound causes half-maximum inhibition of the thymidine incorporation produced by 10% FCS.

TABLE A

| Example No. | $IC_{50}$(nM) |
|---|---|
| 3 | 0.02 |

Investigations of the inhibition of the c-fos gene expression of smooth muscle cells by the compounds according to the invention The antiproliferative action of the compounds was investigated with respect to serum- and growth factor-mediated signal transmission and induction of c-fos gene expression in smooth muscle cell reporter lines. The reporter used here is luciferase, whose expression is controlled by means of the human c-fos promoter. The c-fos promoter/luciferase construct is stably integrated into the chromosomal DNA of the rat smooth muscle cell line A 10 (ATCC CRL 1476). The reporter cells are inoculated into 96-hole plates and cultured at 37° C. for 1–2 days in serum-containing medium (D-MEM with 10% FCS, 2 mM L-glutamine and 15 mM HEPES, pH 7.4) in 5% $CO_2$. To suppress the c-fos promoter activity to basal values, the cells are arrested for 24 hours by withdrawal of serum. Test compounds are then added, and the cells are stimulated with FCS or growth factors to induce luciferase activity. After this treatment period (4 hours) the cells are lysed and their extracts are employed for the determination of luciferase. The $IC_{50}$ values are calculated from the active compound concentration which on sequential dilution of the active compound causes half-maximum inhibition of the luciferase activity produced by the particular stimulus.

In vivo investigations of the inhibition of vascular smooth muscle cell proliferation in the air-perfused rat carotid model The in vivo investigations of the inhibition of vascular smooth muscle cell proliferation in the air-perfused rat carotid model were carded out by the slightly modified method of Fishman et al. (Lab. Invest. 32, 339–351, 1975); operation on the animals was carried out under Nembutal®-anaesthesia. The right common carotid artery is exposed and clamped off with two vessel clamps at a caudal to cranial distance of about 1.5 cm. A cannula is inserted at the cranial end of this vascular segment, and the caudal end is perforated by pricking with a needle. After rinsing with physiological saline solution, a stream of air (25 ml/min for 4 min) is perfused through the segment. The clamps are then removed, the bleeding is stopped with slight pressure and the operation field is closed with wound clamps. The animals are sacrificed eight days after the operation, and the previously air-perfused and, as a control, the corresponding contralateral carotid segments are removed.

The application of the test substances (p.o., i.v., i.p. or s.c.) was started two days before the operation, and the treatment was then carded out over the entire experimental period (duration of treatment in total: 10 days).

The air-induced smooth muscle cell proliferation was determined by means of the DNA content of the carotid segments according to Helms et al. (DNA 43, 39–49, 1985). To do this, the vessel pieces are enzymatically degraded using proteinase K, and the DNA is isolated and determined fluorometrically using bisbenzimide (DNA from herring sperm as standard). The DNA content of the vessels is finally indicated in μg of DNA per mm of carotid.

To determine the antiproliferative action of the compounds according to the invention, a balloon catheter is inserted into the carotid artery of rats and inflated, and the inside of the blood vessel is injured by moving the catheter [Clowes A. W., et at., Lab. Invest. Vol. 49, No. 3, p. 327, 1983]. This injury causes a neointimal smooth muscle proliferation, which causes stenoses. The extent of the vascular constrictions in the animals is determined after about 2 weeks by histological working up of the blood vessels by measuring the surface areas of the proliferation tissue on vascular cross-sections.

The new active compounds can be converted in a known manner into the customary formulations, such as tablets, coated tablets, pills, granules, aerosols, syrups, emulsions, suspensions and solutions, using inert, non-toxic, pharmaceutically active excipients or solvents. The therapeutically active compound should in each case be present here in a concentration from about 0.5 to 90% by weight of the total mixture, i.e. in amounts which are sufficient in order to achieve the dosage range indicated.

The formulations are prepared, for example, by extending the active compounds using solvents and/or excipients, if appropriate using emulsifiers and/or dispersants, it optionally being possible, e.g. in the case of the use of water as a diluent, to use organic solvents as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proved advantageous in the case of intravenous administration to administer amounts of about 0.001 to 20 mg/kg, preferably about 0.01 to 5 mg/kg, of body weight to achieve effective results, and in the case of oral administration the dose is about 0.01 to 50 mg/kg, preferably 1 to 10 mg/kg, of body weight.

In spite of this, if appropriate it may be necessary to depart from the amounts mentioned, namely depending on the body weight or the type of administration mute, on the individual behaviour towards the medicament, the manner of its formulation and the time or interval at which administration takes place. Thus, in some cases it may be sufficient to manage with less than the abovementioned minimum amounts, while in other cases the upper limit mentioned has to be exceeded. In the case of the administration of relatively large amounts, it may be advisable to divide these into several individual doses over the course of the day.

STARTING COMPOUNDS

Example I tert-Butyl trans-2-[4-(2-phenylindol-3-yl-methyl)-phenyl] cyclohexane-1-carboxylate

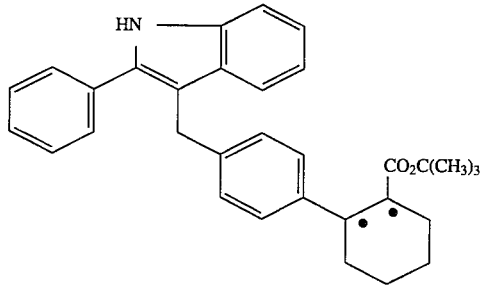

2.8 g (25 mmol) of potassium tert-butoxide are treated dropwise at 0° C. in 20 ml of DMF with a solution of 5.1 g (25 mmol) of 2-phenylindole, and the mixture is stirred for 30 min. A solution of 13.4 g (25 mmol, 60% strength) of tert-butyl trans-2-(p-bromomethylphenyl)cyclohexane-1-carboxylate in 130 ml of DMF is then added dropwise in the come of 30 min and the mixture is brought to room temperature overnight. After concentrating, the residue is taken up in $Et_2O/H_2O$, and the precipitate is separated off and extracted three times with $Et_2O$. After drying over $Na_2SO_4$ and concentrating, the product is purified on silica gel 60 (petroleum ether/ethyl acetate=10:1).

Yield: 2.21 g (19% of theory) $R_f$=0.27 (PE/EA=10:1)

Example II trans-2-[4-(2-Phenylindol-3-yl-methyl)-phenyl]-cyclohexane-1-carboxylic acid

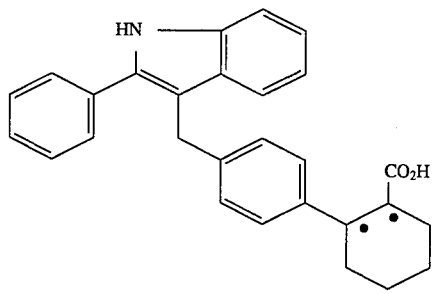

2.2 g (4.7 mmol) of the compound from Example I are stirred at room temperate for 2 h with 15 ml of trifluoroacetic acid in 15 ml of $CH_2Cl_2$. After concentrating, the residue is treated twice with $Et_2O$, the extracts are concentrated, the residue is taken up in $Et_2O$ again, and the solution is extracted once with 0.5N NaOH and twice with $H_2O$ (pH 5). The combined water phases are adjusted to pH 4 using 1N acetic acid and extracted twice with ethyl acetate. The combined ethyl acetate phases are dried over $Na_2SO_4$ and concentrated.

Yield: 1.8 g (100% of theory) $R_f$=0.31 ($CH_2Cl_2$/MeOH/$NH_3$=9:1:0.1)

Example III tert-Butyl trans-2-[4-(1-methyl-2-phenylindol-3-yl-methyl)-phenyl]cyclohexane -1-carboxylate

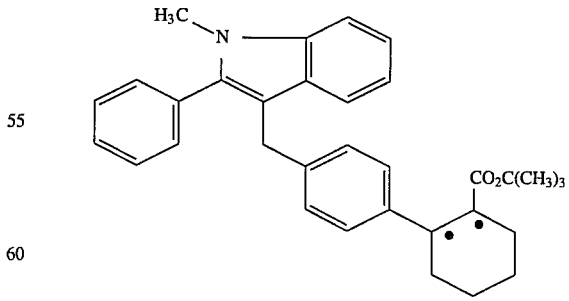

0.4 g (13.2 mmol) of NaH (80%) is suspended in 20 ml of DMF, and the suspension is cooled to 0° C. and treated dropwise with a solution of 5.6 g (12 mmol) of the starting compound from Example I in 50 ml of DMF. After stirring for 30 min, 2.0 g (14.4 mmol) of MeI are added dropwise. After stirring at 0° C. for 1 h, the mixture is slowly warmed to RT and stirred at this temperature for a further 1 h. For working up, the mixture is cautiously treated with water and extracted three times with ethyl acetate. The combined organic phases are dried over $Na_2SO_4$, filtered and concentrated, and the product is chromatographed on silica gel 60 (petroleum ether/ethyl acetate=10:1).

Yield: 1.2 g (40% of theory) $R_f$=0.47 (PE/EA=10:1)

PREPARATION EXAMPLES

Example 1 trans-2-[4-(2-Phenylindol-3-yl-methyl)phenyl]-cyclohexane-1-carbonyl -(L-phenylglycinolamide)

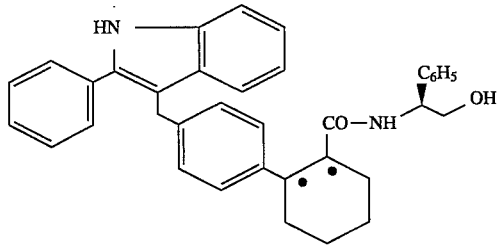

0.14 g (1 mmol) of L-phenylglycinol is treated under argon in 10 ml of $CH_2Cl_2$ with 0.41 g (1 mmol) of the compound from Example II and 0.16 g of 1-hydroxy -1 H-benzotriazole, and the mixture is cooled to −10° C., then treated with 0.3 ml of triethylamine (2 mmol) and 0.23 g (1.2 mmol) of N-(3-dimethylaminopropyl)-N-ethylcarbodiimide hydrochloride and stirred overnight at room temperature. After diluting with $CH_2Cl_2$, the mixture is extracted with $NH_4Cl$, $NaHCO_3$, $H_2O$ and NaCl, dried over $Na_2SO_4$ and concentrated, the product is purified on silica gel 60 ($CH_2Cl_2$/EtOH=100:5).

Yield: 85.4 mg of trans dia B (51.6% of theory) $R_f$=0.44 (CH, $Cl_2$/MeOH=95:5)

The compound shown in Table 1 is prepared in analogy to the procedure of Example 1:

TABLE 1

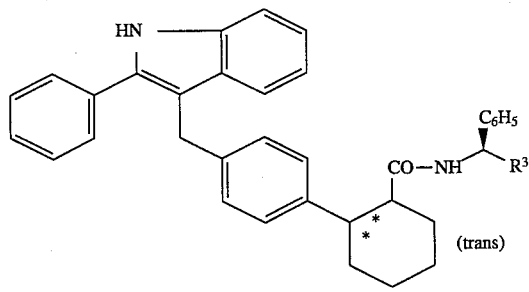

| Ex. No. | $R^3$ | Isomer | $R_f$ (LM) |
|---|---|---|---|
| 2 | $CH_2OH$ | trans dia A (S) | 0.73 ($CH_2Cl_2$/MeOH = 95:5) |

Example 3 trans-2-[4-(2-Phenylindol-3-yl-methyl)phenyl]-cyclohexane -1-carbonyl(phenylglycinamido)amide

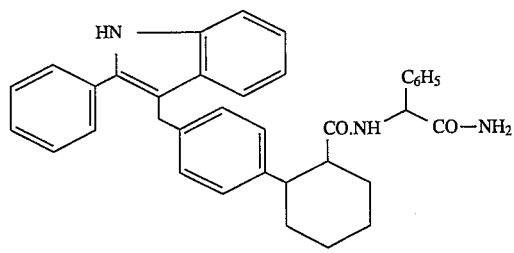

0.16 g (1 mmol) of phenylglycinamide is suspended in 10 ml of $CH_2Cl_2$, treated with 0.41 g (0.1 mmol) of the compound from Example II and 0.16 g (1.1 mmol) of 1-hydroxy-1 H-benzotriazole, the mixture is cooled to −10° C. and, after addition of 0.3 ml of triethylamine and 0.3 g of N-(3-dimethylaminopropyl)-N-ethylcarbodiimide hydrochloride, stirred overnight at room temperature. After diluting with $CH_2Cl_2$, the mixture is shaken with $NH_4Cl$, $NaHCO_3$, $H_2O$ and NaCl, the organic phase is dried over $Na_2SO_4$ and concentrated, and the product is purified on silica gel 60 ($CH_2Cl_2$/EtOH/$NH_3$=100:5:0.1).

Yield: 0.29 g of trans dia B (51.6% of theory) $R_f$=0.3 ($CH_2Cl_2$/MeOH=95:5)

The compound shown in Table 2 is prepared in analogy to the procedure of Example 3:

TABLE 2

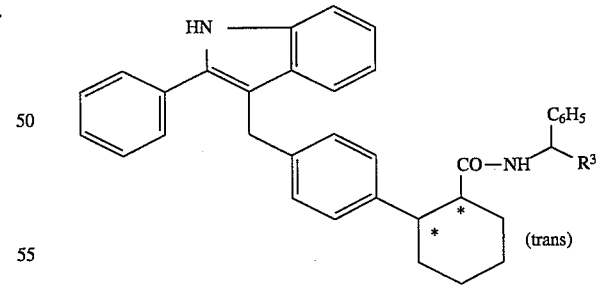

| Ex. No. | $R^3$ | Isomer | $R_f$ (LM) |
|---|---|---|---|
| 4 | $CONH_2$ | trans dia A | 0.49 ($CH_2Cl_2$/MeOH = 95:5) |

The compounds shown in Table 3 are prepared in analogy to the preparation of Examples 1 and 2:

TABLE 3

[structure with H3C-N indole, CH2 linker to phenyl-cyclohexane-CO-NH-CH(C6H5)-R3]

| Ex. No. | R³ | Isomer | R_f (LM) |
|---|---|---|---|
| 5 | CH₂OH | trans dia A (S) | 0.59 (toluene/EA = 1:1) |
| 6 | CH₂OH | trans dia B (S) | 0.31 (toluene/EA = 1:1) |

The compounds shown in Table 4 are prepared in analogy to the preparation of Examples 3 and 4:

TABLE 4

[structure with H3C-N indole, CH2 linker to phenyl-cyclohexane-CO-NH-CH(C6H5)-R3]

| Ex. No. | R³ | Isomer | R_f (LM) |
|---|---|---|---|
| 7 | CONH₂ | trans dia A | 0.33 (toluene/EA = 1:1) |
| 8 | CONH₂ | trans dia B | 0.15 (toluene/EA = 1:1) |

We claim:

1. Substituted indole derivatives of the general formula (I)

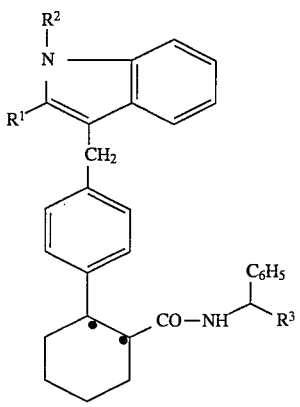

in which

R¹ represents phenyl, cycloalkyl having 3 to 6 carbon atoms or straight-chain or branched alkyl having up to 5 carbon atoms, R² represents straight-chain or branched alkyl having up to 8 carbon atoms, or hydrogen, R³ represents a radical of the formula —CO—NH₂ or —CH₂—OH, and their salts.

2. Substituted indole derivatives of the formula (I) according to claim 1 in which R¹ represents phenyl, cyclopropyl, cyclopentyl, cyclohexyl or straight-chain or branched alkyl having up to 4 carbon atoms, R² represents straight-chain or branched alkyl having up to 6 carbon atoms, or hydrogen, R³ represents a radical of the formula —CO—NH₂ or —CH₂—OH, and their salts.

3. Substituted indole derivatives of the formula (I) according to claim 1 in which R¹ represents phenyl, cyclopropyl, ethyl, iso-propyl or n-butyl, R² represents straight-chain or branched alkyl having up to 5 carbon atoms, or hydrogen, R³ represents a radical of the formula —CO—NH₂ or —CH₂—OH, and their salts.

4. Substituted indole derivative according to claim 1 wherein such compound is 2-[4-(2-Phenylindol-3-yl-methyl)phenyl]-cyclohexane-1 -carbonyl-(L-phenylglycinolamide) of the formula

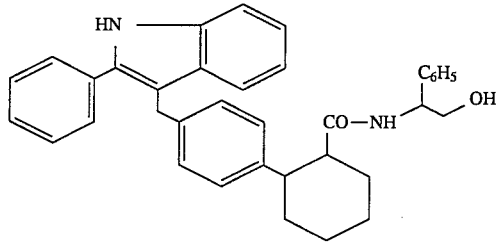

and salts thereof.

5. Substituted indole derivative according to claim 1 wherein such compound is 2-[4-(2-Phenylindol-3-yl-methyl)phenyl]cyclohexane-1-carbonyl(phenylglycinamido)amide of the formula

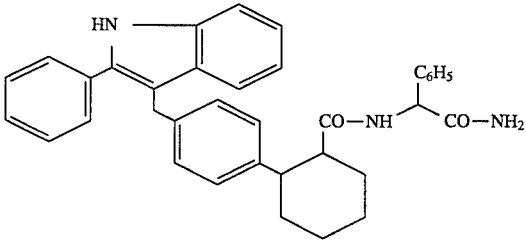

and salts thereof.

6. A composition for the treatment of restenosis comprising an amount effective thereof of the compound or a salt thereof according to claim 1 and a pharmacological acceptable diluent.

7. The method of treating restenosis in a patient in need thereof which comprises administering to such patient an amount effective therefore of a compound or salt thereof according to claim 1.

* * * * *

UNITED STATES PATENT AND TRADEMARK OFFICE
CERTIFICATE OF CORRECTION

PATENT NO. : 5,607,962
DATED : March 4, 1997
INVENTOR(S) : Muller-Gliemann, et al.

It is certified that error appears in the above-indentified patent and that said Letters Patent is hereby corrected as shown below:

```
    Title page, item [30],
    Foreign Application Priority Data:   Delete
" 195 13 176.7 " and substitute
--  195 13 716.7 --
```

Signed and Sealed this

Eighth Day of July, 1997

Attest:

BRUCE LEHMAN

Attesting Officer

Commissioner of Patents and Trademarks